United States Patent
Ren et al.

[11] Patent Number: 5,968,012
[45] Date of Patent: Oct. 19, 1999

[54] BALLOON CATHETER WITH ADJUSTABLE SHAFT

[75] Inventors: Brooke Qin Ren, Champlin; Jon P. St. Germain, Elk River; Scott A. Olson, Zimmerman, all of Minn.

[73] Assignee: Scimed Lifesystems, Inc., Maple Grove, Minn.

[21] Appl. No.: 08/917,075

[22] Filed: Aug. 22, 1997

[51] Int. Cl.$^6$ .................................................. A61M 29/00
[52] U.S. Cl. ............................................. 604/96; 604/103
[58] Field of Search .............................. 604/96, 99, 103, 604/104, 280, 281, 283

[56] References Cited

U.S. PATENT DOCUMENTS 5,316,016   5/1994   Adams et al. ........................ 604/96 X
5,466,230  11/1995   Davila ................................ 604/283 X

*Primary Examiner*—Ronald Stright
*Assistant Examiner*—A. T. Nguyen
*Attorney, Agent, or Firm*—Vidas, Arrett & Steinkraus, P.A.

[57] ABSTRACT

The present invention provides a balloon catheter with a length compensator, which can be an accordion section or a slipping sleeve section. In the accordion section embodiment of the invention, the outer shaft of the catheter includes an accordion section positioned proximally of the balloon. In this embodiment the length compensator is comprised of the accordion section and the outer shaft between the accordion section and the point where the proximal end of the balloon is attached to the outer shaft. The distal end of the balloon is attached to an inner shaft. As the balloon is inflated the accordion section expands to adjust the axial length of the length compensator to compensate for the movement of the two ends of the balloon towards each other. In the slipping sleeve embodiment of the invention, the inner shaft of the catheter includes a slipping sleeve section positioned proximally of the point where the distal end of the balloon is connected to the inner shaft. As the balloon is expanded, the slipping sleeve section contracts, adjusting the axial length of the length compensator to compensate for the shrinkage of the balloon as it expands into contact with the vasculature.

18 Claims, 3 Drawing Sheets

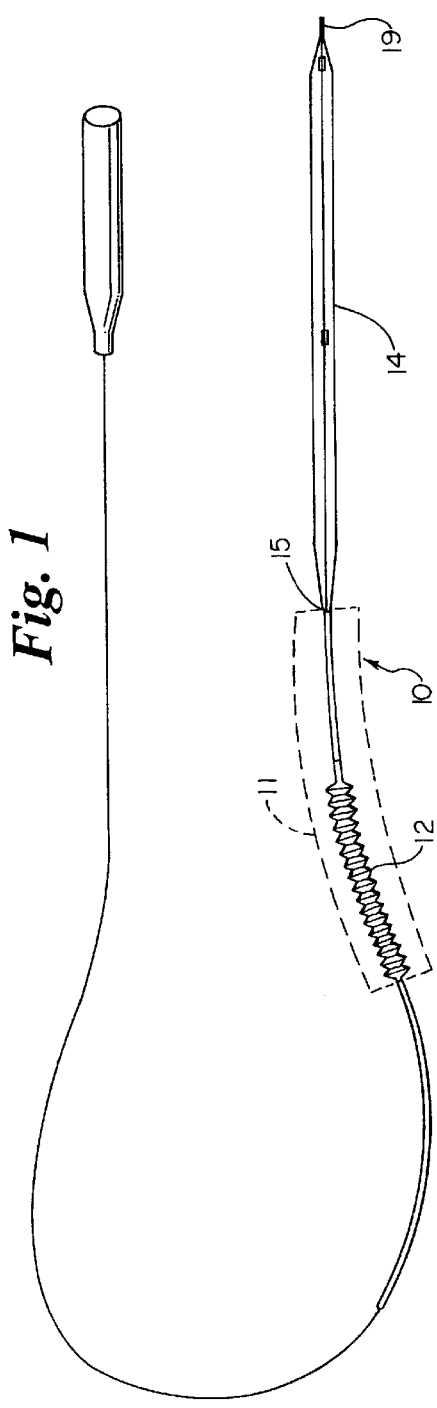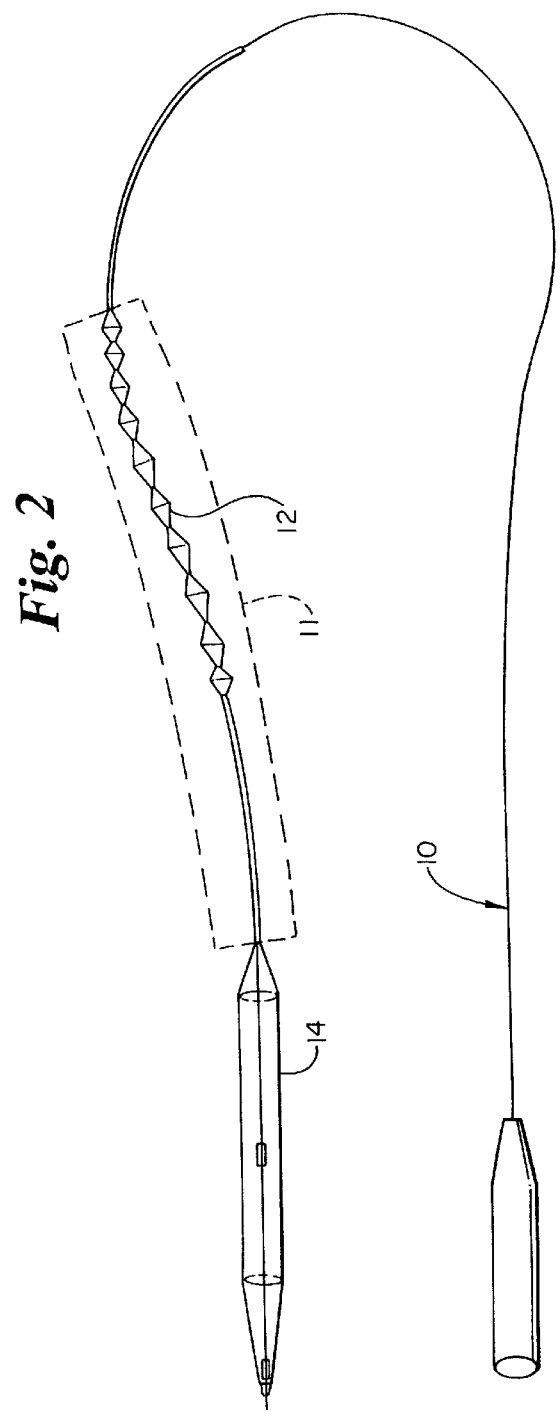

BALLOON CATHETER WITH ADJUSTABLE SHAFT

BACKGROUND OF THE INVENTION

The present invention relates generally to a balloon catheter, and more specifically to a lesion molding balloon catheter.

Applicant is the inventor of an invention entitled "Stent Retrieval Device", filed with the USPTO May 16, 1997 and assigned Ser. No. 08/857,791, the entire contents of which are hereby incorporated by reference. The stent retrieval device utilizes an inventive balloon which will deform 300–400% of the nominal diameter of the balloon at 1 atmosphere.

Applicant has discovered through experimentation that this balloon will also function as a lesion molding balloon in a 3D imaging application. Lesion molding balloons are well known in the art, and expand to conform to the structure of the vasculature. The balloon is then deflated and withdrawn from the body. When the balloon is reinflated it "remembers" its expanded shape, allowing the user to obtain a three dimensional image of the vasculature. An imaging balloon catheter is disclosed in Adams et al U.S. Pat. No. 5,316,016, the entire contents of which are hereby incorporated by reference.

In experimentation, applicant has found that one problem with the extremely compliant inventive balloon is that because it deforms 300–400% of its nominal diameter, it places a great deal of tension on the points it is attached to the outer and inner catheter shafts as it attempts to "shrink". This tension causes the lesion molding balloon to be deformed so that it does not obtain a proper 3D image of the vasculature.

What is needed is a balloon catheter structure which allows use of the inventive lesion molding balloon without having its shape deformed by the tensions of expansion.

SUMMARY OF THE INVENTION

The present invention provides a balloon catheter with a length compensator, which can be an accordion section or a slipping sleeve section. In the accordion section embodiment of the invention, the outer shaft of the catheter includes an accordion section positioned proximally of the balloon. In this embodiment the length compensator is comprised of the accordion section and the outer shaft between the accordion section and the point where the proximal end of the balloon is attached to the outer shaft. The distal end of the balloon is attached to an inner shaft. As the balloon is inflated the accordion section expands to adjust the axial length of the length compensator to compensate for the movement of the two ends of the balloon towards each other.

In the slipping sleeve embodiment of the invention, the inner shaft of the catheter includes a slipping sleeve section positioned proximally of the point where the distal end of the balloon is connected to the inner shaft. As the balloon is expanded, the slipping sleeve section contracts, adjusting the axial length of the length compensator to compensate for the shrinkage of the balloon as it expands into contact with the vasculature.

Depending on the vasculature geometry, the lesion molding balloon may expand from 0–400% of its nominal diameter, resulting in an axial shrinkage of the balloon from 0–40%. Therefore for example, at maximum expansion, an 80 mm uninflated lesion molding balloon with a 1 mm nominal diameter when fully inflated to 4 mm would shrink to an axial length of 48 mm or 40%. The accordion section would expand 32 mm, or the slipping sleeve would contract 32 mm, to compensate for the balloon shrinkage in this example.

BRIEF DESCRIPTION OF THE FIGURES

FIG. 1 shows the first embodiment of the inventive catheter before balloon inflation;

FIG. 2 shows the first embodiment of the inventive catheter after balloon inflation;

DESCRIPTION OF THE PREFERRED EMBODIMENTS

Figure 3:
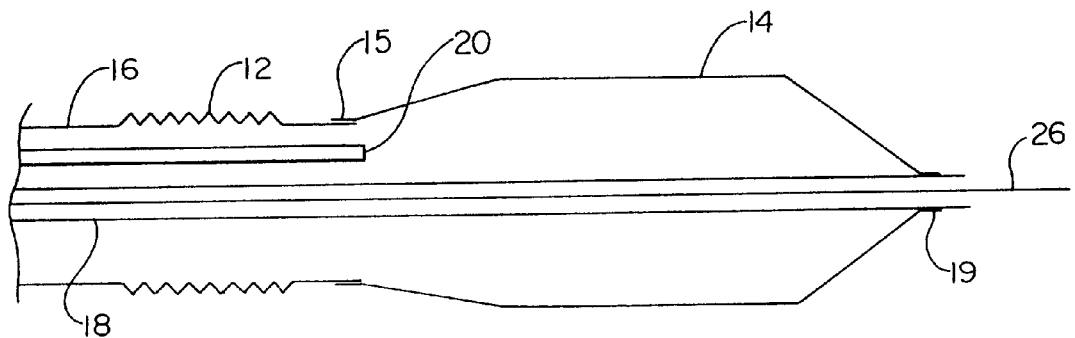
FIG. 3 shows a cross-sectional view of the distal end of the first embodiment inventive catheter.

Referring to FIGS. 1–3, a first preferred embodiment of the inventive catheter is shown generally at 10 with the length compensator 11 being a portion of the outer catheter shaft 16. The length compensator 11 includes an accordion section 12 of the outer shaft 16. The proximal end of inflation lesion molding balloon 14 is connected to the length compensator 11 at attachment point 15 and the distal end of inflation balloon 14 is connected to the inner shaft 18 at point 19. The inner shaft 18 may provide a lumen for guide wire 26. An inflation lumen 20 extends longitudinally in the outer catheter shaft 16 and is used to inflate balloon 14. As balloon 14 is inflated, its attachment points 15 and 19 exert a force toward each other on their respective outer and inner shafts 16 and 18, which causes the accordion section 12 to expand to provide strain relief and compensate for the shrinkage of the lesion molding balloon 14. Expansion of accordion section 12 causes the length compensator 11 to adjust its axial length to compensate for the shrinkage of the axial distance between the two ends of the balloon 15 and 19, as the balloon expands. FIG. 2 shows the catheter 10 with balloon 14 expanded and accordion section 12 expanded.

Figure 4:
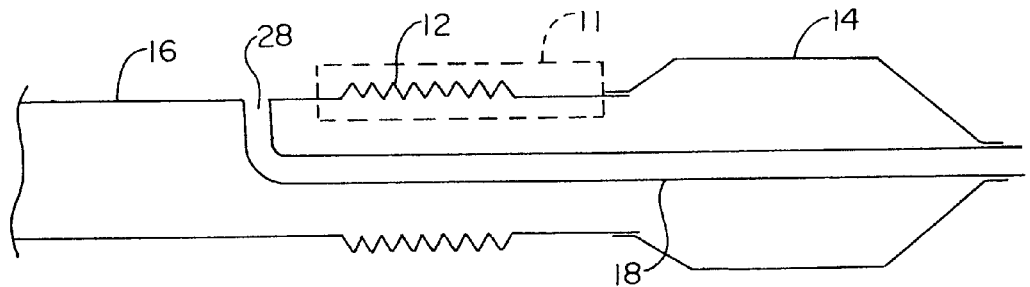
FIG. 4 shows the first embodiment of the invention in an SOE configuration.

The inventive balloon catheter may be utilized in any catheter configuration, such as single operator exchange (SOE), over-the-wire (OTW) or fixed wire. FIG. 4 shows the first embodiment in an SOE configuration. The length compensator 11 may be positioned at any point along the catheter body, but in the SOE version of FIG. 4 must be located distally of the guide wire port 28.

Figure 5:
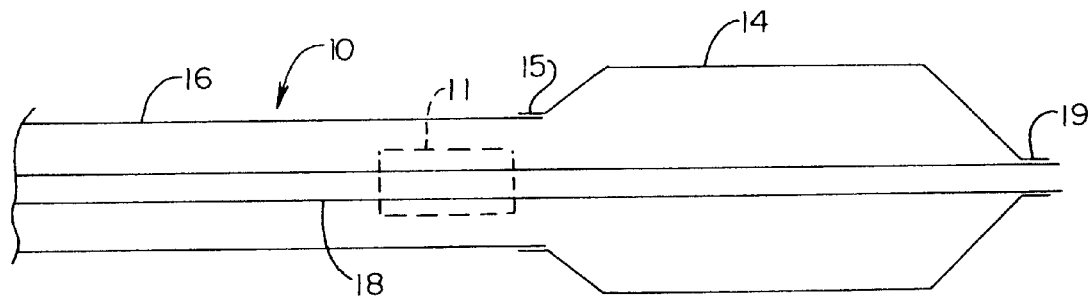
FIG. 5 shows a second embodiment of the inventive catheter before balloon inflation.
Figure 6:
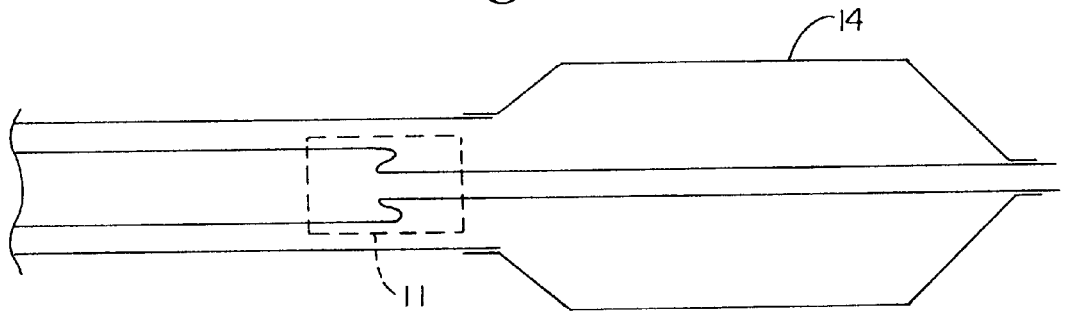
FIG. 6 shows a second embodiment of the inventive catheter after balloon inflation.

Referring to FIGS. 5 and 6, a second embodiment of the inventive catheter is shown generally at 10, with the length compensator 11 being a portion of the inner catheter shaft 18 and including a Teflon slipping sleeve. FIG. 6 shows the catheter 10 with the balloon 14 in the inflated position, which causes the slipping sleeve to collapse, adjusting the axial length of length compensator 11 to compensate for the shrinkage of the axial distance between ends 15 and 19 of the balloon.

Figure 7:
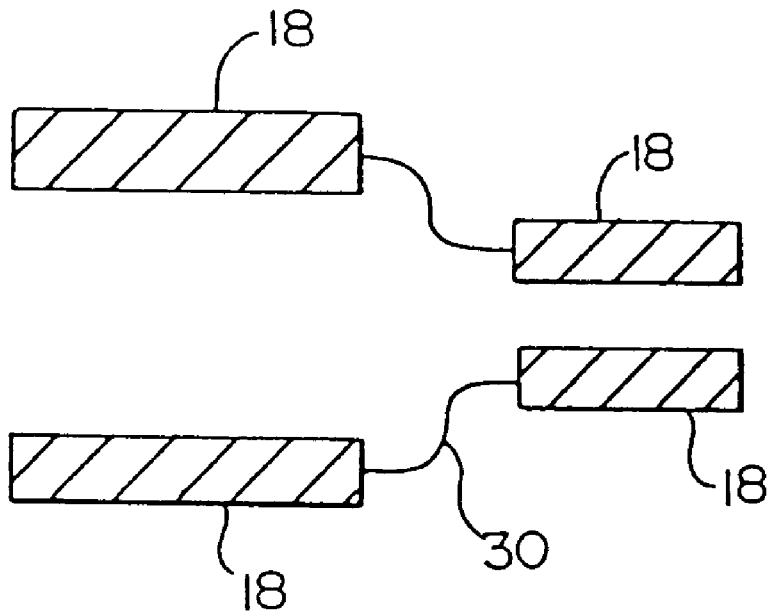
FIG. 7 shows the sliding sleeve section of the inner shaft in the normal expanded position.
Figure 8:
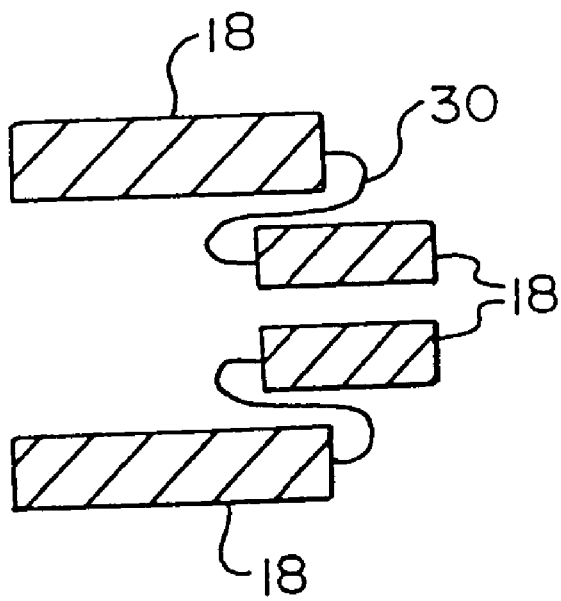
FIG. 8 shows the sliding sleeve section of the inner shaft in the collapsed position.

Referring to FIGS. 7 and 8, a more detailed view of the second embodiment length compensator 11 is shown, in which the inner shaft 18 is in a two-part configuration, with the two parts separated by a Teflon section 30, which adhesively joins the two parts of shaft 18 together in a fluid tight manner. FIG. 7 shows the length compensator in its normal uncollapsed position and FIG. 8 shows the length compensator after the distal part of the inner shaft 18 has slide proximally into the proximal section of inner shaft 18.

It should also be understood that the length compensator 11 could take the form of a slipping sleeve positioned between the distal end of balloon 14 and its attachment point 19 to the inner shaft.

In the preferred embodiment balloon 14 is preferably constructed of semi-crystalline or amorphous blend materials, and more preferably of a blend of PBT and PETG, with a ratio of PBT to PETG ranging from 1:1 to 1:19, by weight, and more preferably with a ratio of 1:3 or 25% PBT and 75% PETG, by weight. The preferred balloon material will deform or yield 300–400% at approximately 1 atmosphere.

In the preferred embodiment accordion 12 is made of Suryln® 9 (a polyolefin copolymer) and must be made of a material sensitive enough to accommodate the balloon shrinkage and yet strong enough not to deform when radial pressure is applied. It is important that the accordion section be configured such that it will expand axially, but that its diameter not increase as the balloons diameter is expanding. Testing has shown that materials having the following properties can be used for the accordion section 12:

flexural modulus: 40,000–250,000 psi;

hardness: 50 D–80 D;

break tensile elongation: above 50%;

tensile strength: 6,000–9,000 psi, and burst pressure of at least 5 atmospheres.

In addition to Suryln® 9, low water absorption polyamide and its copolymer, polyester and its copolymer, polyurethane, polyvinyl chloride, low density polyethylene, high density polyethylene and any other material meeting the preceding properties may be used for the accordion material 12.

It has been found experimentally that the thickness of the accordion material 12 is very important and for the preferred material, Suryln® 9, the thickness must be in the range of 0.0005 inches to 0.003 inches thick (one wall). It is important that the force required to expand the accordion section 12 be low enough not to affect the expansion of balloon 14. In testing of the preferred embodiment a stretch force of as low as 2 grams has been observed. The preferred embodiment also allows for axial longitudinal growth of up to 100%, although this parameter can easily be adjusted as desired by varying the depth of the folds or the material properties. In the preferred embodiment the axial length of accordion section 12 is 40 mm, but it should be understood that this can also be varied as desired.

The accordion section 12 may be separately made and adhesively attached to the outer shaft 16 or the outer shaft 16 may be processed into the accordion structure. U.S. Pat. No. 5,534,007 issued Jul. 9, 1996 entitled "Stent Deployment Catheter With Collapsible Proximal Sheath" and "Stent Deployment Catheter With Collapsible Sheath", filed May 17, 1996 as Ser. No. PCT/U.S.96/07143 and published Nov. 21, 1996 as WO 96/36298 both disclose outer shafts with accordion sections, and the entire contents of both are hereby incorporated by reference.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A balloon catheter comprising:

an elongate catheter body including first and second shafts and an inflation lumen, each shaft having proximal and distal ends;

an inflatable balloon having first and second ends, the first end of the balloon being connected to the distal end of the first shaft and the second end of the balloon being connected to the distal end of the second shaft, the inflatable balloon being in fluid communication with the inflation lumen;

the second shaft comprising a length compensator, the length compensator allowing a portion of the second shaft to move axially relative to the other portion to adjust the length of the second shaft as the balloon is inflated, which reduces the axial length of the balloon.

2. The balloon catheter of claim 1 wherein the first shaft is an outer shaft and the second shaft is the inner shaft, the inner shaft being carried within the outer shaft and a portion of the inner shaft extending beyond the distal end of the outer shaft, and wherein the inflatable balloon has proximal and distal ends, the first end of the inflatable balloon being the proximal end and the second end of the inflatable balloon being the distal end.

3. The balloon catheter of claim 2 wherein the length compensator comprises an accordion section of the outer shaft positioned proximally to the inflatable balloon, wherein as the inflatable balloon expands the accordion section expands, thereby lengthening the outer shaft.

4. The balloon catheter of claim 1 wherein the second shaft is an outer shaft and the first shaft is the inner shaft, the inner shaft being carried within the outer shaft and a portion of the inner shaft extending beyond the distal end of the outer shaft, and wherein the inflatable balloon has proximal and distal ends, the first end of the inflatable balloon being the distal end and the second end of the inflatable balloon being the proximal end.

5. The balloon catheter of claim 4 wherein the length compensator comprises a slipping sleeve section of the inner shaft positioned proximally of the distal end of the balloon, wherein as the inflatable balloon expands the slipping sleeve section contracts, thereby shortening the inner shaft.

6. The balloon catheter of claim 1 wherein the catheter body is configured as a single operator exchange (SOE) catheter.

7. The balloon catheter of claim 1 wherein the catheter body is configured as an over the wire (OTW) catheter.

8. The balloon catheter of claim 1 wherein the catheter body is configured as a fixed wire catheter.

9. The balloon catheter of claim 1 wherein the length compensator includes an accordion section of the catheter body.

10. The balloon catheter of claim 9 wherein the accordion section is constructed of a material having a flexural modulus in the range of 40,000 to 250,000 psi, a hardness in the range of 50 D to 80 D, break tensile elongation above 50%, and a tensile strength in the range of 6,000 to 9,000 psi.

11. The balloon catheter of claim 10 wherein the accordion section is constructed of a polyolefin copolymer.

12. The balloon catheter of claim 1 wherein the length compensator includes a slipping sleeve section of the catheter body.

13. The balloon catheter of claim 1 wherein the balloon is a lesion molding balloon for obtaining a 3D image of the vasculature.

14. The balloon catheter of claim 13 wherein the balloon is constructed of a blend of polybutylene terephthalate (PBT) and glycol-modified polyethylene terephthalate (PETG).

15. The balloon catheter of claim 14 wherein the ratio of PBT to PETG ranges from 1:1 to 1:19 by weight.

16. The balloon catheter of claim 15 wherein the ratio of PBT to PETG is 1:3 by weight.

17. The balloon catheter of claim 1 wherein the balloon will deform 300–400% of the nominal diameter of the balloon at 1 atmosphere.

18. The balloon catheter of claim 17 wherein the accordion section is constructed of a material having a flexural modulus in the range of 40,000 to 250,000 psi, a hardness in the range of 50 D to 80 D, break tensile elongation above 50%, and a tensile strength in the range of 6,000 to 9,000 psi.

* * * * *